(12) United States Patent
Takahashi et al.

(10) Patent No.: US 11,662,348 B2
(45) Date of Patent: May 30, 2023

(54) METHOD FOR DETECTING CONSTITUENT COMPONENT OF ANTIBODY-DRUG CONJUGATE

(71) Applicant: Konica Minolta, Inc., Tokyo (JP)

(72) Inventors: Masaru Takahashi, Kokubunji (JP); Takeshi Shiraishi, Kunitachi (JP); Noboru Koyama, Niiza (JP)

(73) Assignee: KONICA MINOLTA, INC., Tokyo (JP)

( * ) Notice: Subject to any disclaimer, the term of this patent is extended or adjusted under 35 U.S.C. 154(b) by 602 days.

(21) Appl. No.: 16/481,013

(22) PCT Filed: Feb. 2, 2018

(86) PCT No.: PCT/JP2018/003599
§ 371 (c)(1),
(2) Date: Jul. 25, 2019

(87) PCT Pub. No.: WO2018/159212
PCT Pub. Date: Sep. 7, 2018

(65) Prior Publication Data
US 2020/0003778 A1 Jan. 2, 2020

(30) Foreign Application Priority Data
Feb. 28, 2017 (JP) .............................. JP2017-036438

(51) Int. Cl.
| | | |
|---|---|---|
| *G01N 33/574* | (2006.01) | |
| *G01N 33/58* | (2006.01) | |
| *G01N 33/483* | (2006.01) | |
| *G01N 21/64* | (2006.01) | |
| *A61K 47/69* | (2017.01) | |

(52) U.S. Cl.
CPC ....... *G01N 33/574* (2013.01); *G01N 21/6458* (2013.01); *G01N 33/4833* (2013.01); *G01N 33/582* (2013.01); *A61K 47/6921* (2017.08); *A61K 47/6929* (2017.08); *G01N 21/6428* (2013.01); *G01N 21/6486* (2013.01); *G01N 2021/6441* (2013.01)

(58) Field of Classification Search
CPC ............. G01N 33/574; G01N 21/6458; G01N 33/4833; G01N 33/582; G01N 21/6428; G01N 21/6486; G01N 2021/6441; G01N 33/587; A61K 47/6921; A61K 47/6929
See application file for complete search history.

(56) References Cited

U.S. PATENT DOCUMENTS

2013/0157287 A1 6/2013 Takanashi et al.
2014/0186857 A1 7/2014 Takanashi et al.

FOREIGN PATENT DOCUMENTS

| WO | WO2012/029342 A1 * | 3/2012 |
|---|---|---|
| WO | 2013/035703 A1 | 8/2012 |
| WO | 2012/133047 A1 | 10/2012 |
| WO | 2012/029752 A1 | 3/2013 |

OTHER PUBLICATIONS

Hikage et al., Nanotechnology, 21:185103, 2010 (Year: 2010).*
Gonda et al., Biochemical and Biophysical Research Comms, 426:409-414, 2012 (Year: 2012).*
Akkapeddi et al., Chem. Sci., 7, 2954, 2016 (Year: 2016).*
Shukla et al., Nanotechnology, 2008: 19(29): 295102 (Year: 2008).*
JPO, Office Action for the corresponding Japanese Patent Application No. 2018-568978, dated Mar. 19, 2019, with English translation (9 pages).
Ryan, M. C., et al., "Therapeutic Potential of SGN-CD19B, a PBD-based Anti-CD19 Drug Conjugate, for Treatment of B-cell Malignancies," Blood, Nov. 2017, pp. 2018-2026, vol. 18, No. 130.
PCT, Written Opinion of the International Searching Authority for the corresponding international application No. PCT/2018/003599, dated Apr. 24, 2018, with English translation (9 pages).
PCT, International Search Report for the corresponding international application No. PCT/2018/003599, dated Apr. 24, 2018, with English translation (4 pages).
Smith, L.M. et al., "Potent Cytotoxicity of an Auristatin-containing Antibody-drug Conjugate Targeting Melanoma Cells Expressing Melanotransferrin/p97," Molecular Cancer Therapeutics, Jun. 2006, vol. 5, No. 6, pp. 1474-1482.
Ponte, J.F. et al., "Mirvetuximab Soratansine (IMGN853), a Folate Receptor Alpha-Targeting Antibody Drug Conjugate, Potentiates the Activity of Standard of Care Therapeutics in Ovarian Cancer Models," Neoplasia, Dec. 2016, vol. 18, No. 12, pp. 775-784.
Kouki Yuko et al., "FISH analysis—effectiveness and points of caution, comparison with immunohistochemistry," Clinical Laboratory, 2006, vol. 50, No. 7, pp. 753-760 (English translation not available; document showing a well-known art that has been newly presented).
JPO, Office Action for the corresponding Japanese Patent Application No. 2018-568978, dated Jul. 24, 2019, with English translation (11 pages).
EPO, Extended European Search Report for the corresponding European application No. 18761634.7, dated Jan. 3, 2020 (6 pages).
CNIPA, Office Action for the corresponding Chinese application No. 201880013679.4, dated Mar. 15, 2022, with English translation.
Office Action dated Jan. 9, 2023 for the corresponding Chinese Application No. 201880013679.4, with English translation.

* cited by examiner

*Primary Examiner* — Stacey N MacFarlane
(74) *Attorney, Agent, or Firm* — Lucas & Mercanti, LLP

(57) ABSTRACT

The present invention relates to a method for detecting an antibody-drug-conjugate and relates to a method for determining the efficacy of an antibody-drug-conjugate with high accuracy by a quantitative technique for identifying an expression level of a target molecule in a target cell of the antibody-drug-conjugate and interactions therebetween. According to the method, visualizing a drug and an antibody, or components of an antibody-drug-conjugate, by immunostaining with a phosphor integrated dot enables detection of the antibody-drug-conjugate and the components.

8 Claims, 2 Drawing Sheets

METHOD FOR DETECTING CONSTITUENT COMPONENT OF ANTIBODY-DRUG CONJUGATE

CROSS REFERENCE TO RELATED APPLICATION

This Application is a 371 of PCT/JP2018/003599 filed on Feb. 2, 2018 which, in turn, claimed the priority of Japanese Patent Application No. 2017-036438 filed on Feb. 28, 2017, both applications are incorporated herein by reference.

TECHNICAL FIELD

The present invention particularly relates to a method for detecting an antibody and/or a drug, that is, a component(s) of an antibody-drug-conjugate.

BACKGROUND ART

Cancer is a disorder that shares the cause of adult death with vascular disorders such as myocardial infarction and cerebral infarction. For example, the incidence of breast cancer is lower in Japan than in Western countries but has increased in recent years. In 1998, the incidence of breast cancer surpassed the incidence of gastric cancer and ranked number one in Japanese women with cancer. According to a recent report from the Ministry of Health, Labor and Welfare, in 2005, the yearly incidence of breast cancer exceeded 50,000. Year by year, the number of individuals with breast cancer is escalating worldwide. According to WHO Report, in 2008, breast cancer ranked number one even when adding up the number of men and women with cancer, and the yearly incidence of breast cancer exceeded 1.38 million, about 23% of all women with cancer.

In the related art, payloads have been widely used as therapeutic agents for cancer. However, in recent years, a large number of antibody drugs with high selectivity and therapeutic effects and with few side effects has been developed and used clinically. More recently, the development of an antibody-drug-conjugate (ADC) that combines advantages of payloads and antibody drugs has been started, and ADCs are recognized as an attractive developable field for cancer treatment.

An ADC has a structure in which a monoclonal antibody and a drug such as a payload are linked through an appropriate linker. When the ADC specifically binds to an antigen such as a cell surface antigen, a receptor, or a ligand expressed on a target cell surface, and when the ADC is incorporated into a cell through endocytosis, the linker and the antibody are degraded due to an intracellular pH environment and an enzyme. Accordingly, the drug is freed from the antibody, which enables selective killing of a cell of interest.

To establish an effective dosage regimen in clinical use of ADCs, and to expand subjects for administration, it is desirable to specify pharmacokinetics of ADCs at different points after administration. However, from the aspect of sensitivity, it is difficult to detect ADCs by techniques in the related art.

Furthermore, as a method for determining the efficacy of an ADC, it is desirable to specify information such as an interaction with a target cell. For example, to make an ADC effective against a tumor, it is required that a target molecule of the ADC should be sufficiently expressed on a tumor cell surface of a patient and that the ADC should appropriately recognize and interact with the target molecule so as to be incorporated into the cell. Accordingly, quantitative assessment of an expression level of a biological substance, which is to be a target of an ADC, makes it possible to efficiently determine applicability of a molecular target drug for each patient.

With regard to antibody drugs, as a method for determining the efficacy of trastuzumab (trade name; Herceptin (registered trademark)), or a typical anticancer agent for breast cancer, analysis of expression information of HER2 protein, or a target molecule, is in widespread use. Examples of such a method widely used in clinicals include immunohistochemistry (IHC) for staining a protein of a target biological substance, and fluorescence in situ hybridization (FISH) for staining a target biological substance gene.

In IHC, 3,3'-diaminobenzidine (DAB) is used to stain and detect HER2 protein contained in a sample. However, a staining level is roughly determined on a four-scale out of 0 to 3 and is less quantitative. Furthermore, a criterion for determining the staining level depends on the proficiency of a pathologist. These are clinical problems.

In FISH, a probe for detecting a gene that encodes HER2 protein on the 17th chromosome is used to fluorescently stain the gene. Although FISH is a quantitative inspection, FISH is not a method for directly assessing an amount and intracellular localization of HER2 protein.

In order to assess an expression level and intracellular localization of a protein more accurately, the following staining technique has been recently proposed and put to practical use: a protein of interest is labeled with a nanosized fluorescent particle, that is, for example, a phosphor integrated dot (PID) which contains resin as the matrix and integrated phosphors such as fluorochromes and quantum dots. The protein of interest is labeled by the PID (which may also be referred to as "fluorescent substance-integrated nanoparticle" or "phosphor-containing particle" in other literatures) and irradiated with excitation light compatible with fluorescent substances integrated inside the particle, which enables observation of the protein of interest as a bright spot with high luminance. Furthermore, the protein of interest is less likely to be decolored, which enables imaging for a relatively long period. For example, Patent Literature 1 and Patent Literature 2 disclose immunostaining with a PID. Furthermore, Patent Literature 3 discloses IHC in which an antibody (such as trastuzumab) used for an antibody drug labeled by a PID is labeled with a PID and is bound to an antigen (such as HER2) targeted by the antibody drug. Patent Literature 3 also describes that such a technique is applicable to a method for determining the efficacy of an antibody drug.

CITATION LIST

Patent Literature

Patent Literature 1: WO 2013/035703 A
Patent Literature 2: WO 2012/029752 A
Patent Literature 3: WO 2012/133047 A

SUMMARY OF INVENTION

Technical Problem

The present invention has been made in light of the problems, and an object of the present invention is to provide a method for detecting an ADC and provides to a method for determining the efficacy of an ADC with high accuracy by a quantitative technique for identifying an expression level of a target molecule in a target cell of the ADC and interactions therebetween.

Solution to Problem

The inventors of the present invention have found that it is possible to visualize the disposition of an ADC by immunostaining using an antibody that specifically recognizes a drug and antibody, or components of the ADC, and using a fluorescent nanoparticle such as a PID.

In another embodiment, the present invention provides a method for acquiring information for diagnosis or treatment to identify information associated with, for example, an average expression level per cell of a target molecule expressed on a cell targeted by an ADC, localization of the ADC (whether the ADC is incorporated into a target cell), and a ratio of a target molecule bound to the ADC to the total amount of target molecules.

In other words, the present invention provides the following method for detecting an ADC and method for acquiring information associated with the ADC.

[Article 1]

A method for detecting a component of an ADC by immunostaining using a PID, the method including at least one of the following (a) and (b): (a) visualizing a drug which is a component of the ADC; and (b) visualizing an antibody which is a component of the ADC.

[Article 2]

The method for detecting a component of an ADC according to Article 1, further including (c) visualizing a target molecule of the ADC.

[Article 3]

The method for detecting a component of an ADC according to Article 2, wherein the target molecule is a protein expressed on a cell.

[Article 4]

The method for detecting a component of an ADC according to Article 2 or 3, wherein the target molecule is a receptor or a ligand expressed on a cell surface.

[Article 5]

The method for detecting a component of an ADC according to Article 3 or 4, wherein the cell is a cancer cell or an immune cell.

[Article 6]

The method for detecting a component of an ADC according to any one of Articles 2 to 5, wherein the target molecule is selected from the group consisting of a protein in an immune system, a cancer cell growth factor, a metastasis inhibitory factor, a vascular growth factor, a cytokine, a cancer cell growth inhibitory factor receptor, a metastasis inhibitory factor receptor, a vascular growth factor receptor, and a cytokine receptor in a cancer cell.

[Article 7]

The method for detecting a component of an ADC according to any one of Articles 2 to 5, wherein the target molecule is selected from the group consisting of a protein in an immune system, a growth factor, a growth inhibitory factor, a growth stimulatory factor, an immune cell migration factor, a cytokine, an immune system inhibitory factor, a signal-transducing protein, and receptors thereof in an immune cell.

[Article 8]

A method for acquiring information for diagnosis or treatment of a disorder by the method for detecting a component of an ADC according to any one of Articles 1 to 7, wherein the method for acquiring information employs a sample collected from a human or non-human animal to which an ADC administered, and the method for acquiring information specifies at least one piece of information associated with (i) localization of the ADC, (ii) a ratio of a target molecule bound to the ADC to a total amount of target molecules, and (iii) distances between the target molecule, an antibody which is a component of the ADC, and a drug which is a component of the ADC.

[Article 9]

The method for acquiring information according to Article 8, wherein the information for diagnosis or treatment is associated with cancer, a neurological disorder, an infectious disorder, or a hereditary disorder.

[Article 10]

The method for acquiring information according to Article 8 or 9, wherein the sample is derived from a tumor tissue.

Advantageous Effects of Invention

According to an aspect of the present invention, a PID or the like is preferably used to visualize an ADC in a quantitative manner with high accuracy. This technique enables specification of intracellular localization and pharmacokinetics of the ADC which are not specified by an assessment in the related art which employs DAB or the like. Furthermore, this technique makes possible to confirm an interaction of the ADC with a predetermined type of cell and localization of the ADC.

According to another aspect of the present invention, information associated with, for example, intracellular localization of the ADC and an expression level of a predetermined type of protein in a predetermined type of cell are combined. Accordingly, it is possible to acquire information useful for diagnosis or treatment of disorders, relating to cancer or the like, with an ADC. Furthermore, combining some pieces of information other than the above (factors) enables more accurate selection of a patient who is suitable for administration and enables planning of an appropriate dosage regimen.

DESCRIPTION OF EMBODIMENTS

Figure 1:
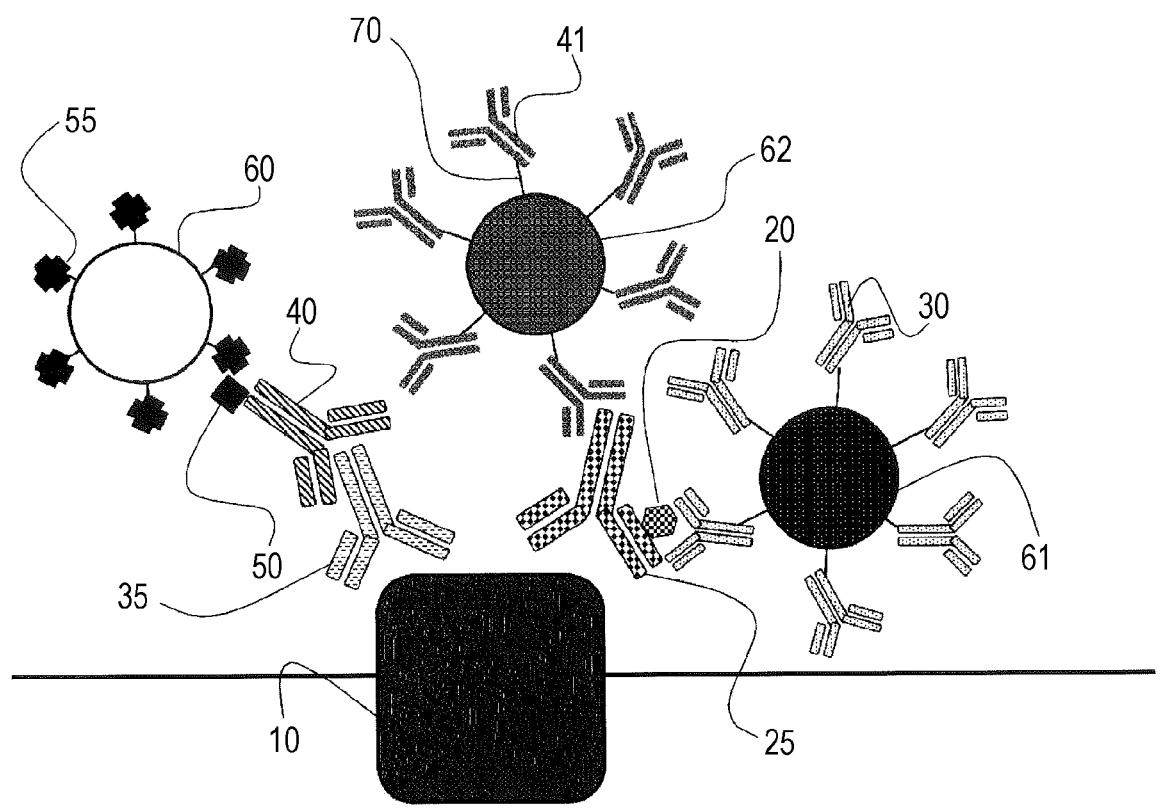
FIG. 1 is a schematic view of trichrome staining performed in Example 2.

A "method for detecting an ADC" according to the present invention employs a sample obtained from a human or a non-human animal to which an ADC is administered, and the method includes quantifying localization of the ADC on the sample.

<Antibody-Drug-Conjugate>

An "ADC" contains at least an "antibody", a "drug," and a "linker" as components, and the drug is linked to the antibody through the linker. Optionally, a spacer may be present between the antibody and the linker, or between the linker and the drug. Typically, an ADC has the following structure; (antibody)-(any spacer)-(linker)-(any spacer)-(drug).

The "ADC" is not particularly limited but is selected from substances which have a low clearance rate and a low metabolic rate in blood or in non-target tissues and which are restricted from being transported into non-target cells.

Specific examples of the "ADC" include trastuzumab emtansine (trade name; Kadocyla) in which emtansine, a cytotoxic substance, binds to humanized HER2 antibody trastuzumab (Herceptin), Brentuximab vedotin (trade name; Adcetris) in which monomethyl auristatin E, a microtubule inhibitor, binds to an anti-CD30 monoclonal (mouse human chimera) antibody, and gemtuzumab ozogamicin (trade name; Mylotarg).

As the "antibody," a component of the ADC (which may be referred to herein as "ADC constituent antibody"), the method may employ a primary antibody (IgG) that specifically recognizes and binds to a target molecule of the ADC as an antigen. A secondary antibody (IgG) that specifically recognizes and binds to the primary antibody may also be used as a component of the ADC. In this case, note that it is required to administer the secondary antibody together with the primary antibody.

The "drug," a component of the ADC (which may be referred to herein as "ADC constituent drug"), is not particularly limited and preferably has an antitumor effect, cellular cytotoxicity, an anti-angiogenic effect, or an anti-inflammatory therapeutic activity.

Examples of the drug include a compound, a polypeptide, a protein, a nucleic acid, an antibiotic, and a virus. The drug may have a target (for example, a receptor) or an extracellular or intracellular site of action. The drug may also include a penetrating peptide sequence such as the sequence described in U.S. Ser. No. 10/231,889 A. For example, the drug may include a drug selected from the following drug group having antitumor therapeutic activity: *vinca* alkaloids such as vincristine, vinblastine, vindesine, vinorelbine; taxanes or taxoids such as paclitaxel, docetaxel, 10-deacetyl taxol, 7-epi-taxol, baccatin III, xylosyl taxol; alkylating agents such as ifosfamide, melphalan, chloroaminophen, procarbazine, chlorambucil, thiophosphoramide, busulfan, dacarbazine (DTIC), mitomycin C-containing mitomycin, nitroso-urea, and derivatives thereof (for example, estramustine, BCNU, CCNU, and fotemustine); platinum derivatives such as cisplatin (for example, carboplatin and oxaliplatin); antimetabolites such as methotrexate, aminopterin, 5-fluorouracil, 6-mercaptopurine, larchitrexed, cytosine arabinoside (or cytarabine), adenosine arabinoside, gemcitabine, cladribine, pentostatin, fludarabine phosphate, and hydroxyurea; inhibitors of topoisomerase I or II such as camptothecin derivatives (for example, irinotecan and topotecan or 9-dimethylaminomethyl-hydroxy-camptothecin hydrochloride), epipodophyllotoxins (for example, etoposide and teniposide), and amsacrine; mitoxantrone; L-canavanine; antibiotics such as anthracyclines and adriamycin or doxorubicin, THP-adriamycin, daunorubicin, idarubicin, rubidazone, pirarubicin, zolubicin, analogues of aclarubicin and anthracycline, epiadriamycin (4'-epiadriamycin or epirubicin) and mitoxantrone, bleomycin, actinomycin D-containing actinomycin, streptozotocin, calicheamicin, duocarmycin, and combretastatin; L-asparaginase; hormones; pure inhibitors of aromatase; analogous antagonists of androgen and LH-RH; cytokines such as interferon alpha (IFN-alpha), interferon gamma (IFN-gamma), interleukin 1 (IL-1)), IL-2, IL-4, IL-6, IL-10, IL-12, IL-15, tumor necrosis factor-alpha (TNF-alpha), insulin-like growth factor (IGF)-1 antagonist; proteasome inhibitors; farnesyl-transferase inhibitors (FTI); epothilone; maytansinoids; discodermolide; fostryesin; antibodies; inhibitors of tyrosine kinase such as STI571 (imatinib mesylate); endostatin; proteins, peptides, and anti-inflammatory cytokines; and pharmaceutically acceptable base addition salts or acid addition salts, hydrates, solvates, precursors, metabolites, or stereoisomers thereof.

The "linker" is not particularly limited but is preferably a peptide chain cleavable by at least one enzyme in a target cell. The present invention may employ linkers having various lengths. Note that a linker having at least three amino acids is preferable, and a linker with three to eight amino acids is particularly preferable.

The "spacer" is not particularly limited. Examples of the "spacer" include bifunctional and polyfunctional organic radicals independently selected from substituted or unsubstituted alkyl, substituted or unsubstituted heteroalkyl, substituted or unsubstituted aryl, substituted or unsubstituted heteroaryl, aldehydes, acids, esters, ethers, thioethers, anhydrides, and sulfhydryl groups or carboxyl groups, for example, maleimide derivatives, maleimide cyclohexane derivatives, maleimide benzoic acid derivatives, and maleimidecaproic acid derivatives. Alternatively, the "spacer" may be derived from, for example, cyanogen bromide or cyanogen chloride, succinimidyl ester, or sulfonic acid halide.

<Method for Detecting Antibody-Drug-Conjugate>

A method for detecting a component of an ADC according to the present invention is carried out by immunostaining using a fluorescent PID having an intensity high enough to express a molecule one by one as a bright spot. The method includes (a) visualizing a drug which is a component of the ADC; and (b) visualizing an antibody which is a component of the ADC.

The step (a), visualizing a drug which is a component of the ADC (ADC constituent drug), may be carried out by general immunostaining using an IgG which specifically recognizes and binds to the drug (which is referred to herein as "antibody A") and to which a PID binds. For example, when detecting an ADC that contains emtansine, or a tubulin polymerization inhibitor, as a component, immunostaining may be performed by a general method using an anti-emtansine antibody labeled by a PID as a stain.

The step (b), visualizing an antibody which is a component of the ADC (ADC constituent antibody), may be carried out by general immunostaining using, as a stain, an IgG which specifically recognizes and binds to the ADC constituent antibody as an antigen (which is referred to herein as "antibody B") and to which a PID as a labeling material is bound.

<Quantification of Target Molecule>

It is preferred that the method for detecting a component of an ADC according to the present invention should further include (c) visualizing a target molecule of the ADC. The target molecule herein is a protein expressed on a target cell of the ADC. Examples of the target cell include a cancer cell, an immune cell, a stromal cell (for example, fibroblast, endothelial cell, and white blood cell (lymphocyte, monocyte, neutrophil, eosinophil, basophil)). The target molecule is not particularly limited as long as it is a protein expressed on a target cell. Preferably, the target molecule is a protein expressed on a cancer cell and on an immune cell, and more preferably, the target molecule is a receptor or a ligand expressed on a cell surface.

Examples of the protein expressed on a cancer cell include a protein in an immune system, a cancer cell growth factor, a metastasis inhibitory factor, a vascular growth factor, a cytokine, a cancer cell growth inhibitory factor receptor, a metastasis inhibitory factor receptor, a vascular growth factor receptor, and a cytokine receptor.

Specific examples of the protein expressed on a cancer cell include CD40, TL1A, GITR-L, 4-188-L, CX4D-L, CD70, HHLA2, ICOS-L, CD85, CD86, CD80, MHC-II, PDL1, PDL2, VISTA, BTNL2, B7-H3, B7-H4, CD48, HVEM, CD40L, TNFRSF25, GITR, 4-188, OX40, CD27, TMIGD2, ICOS, CD28, TCR, LAG3, CTLA4, PD1, CD244, TIM3, BTLA, CD160, LIGHT, EGFR (HER1), HER2, HER3, HER4, IGFR, HGFR, VEGF-A, VEGF-B, VEGF-C, VEGF-D, VEGF-E, P1GF-1, P1GF-2, G-CSF, M-CSF, EPO, SCF, EGF, FGF, IGF, NGF, PDGF, TGF, ACTG2, ALDOA, APC, BRMS1, CADM1, CAMK2A, CAMK2B, CAMK2D, CCL5, CD82, CDKN1A, CDKN2A, CHD4, CNN1, CST7, CTSL, CXCR2, YBB, DCC, DENR, DLC1, EGLN2, EGLN3, EIF4E2, EIF4EBP1, ENO1, ENO2, ENO3, ETV4, FGFR4, GSN, HK2, HK3, HKDC1, HLA-DPB1, HUNKIL11, KDM1A, KISS1, LDHA, LIFR, MED23, MET, MGAT5, MAP2K4, MT3, MTA1, MTBP, MTOR, MYCL, MYH11, NDRG1, NF2, NFKB1, NME1, NME4, NOS2, NR4A3, PDK1, PEBP4, PFKFB1, PFKFB4, PGK1, PLAUR, PTTG1, RB1, RORB, SET, SLC2A1, SNRPF, SSTR2, TCEB1, TCEB2, TCF20, TF, TLR4, TNFSF10, TP53, TSHR, MMP2, MMP, MMP10, and HIF 1.

Examples of the protein expressed on an immune cell include a protein in an immune system, a growth factor, a growth inhibitory factor, a growth stimulatory factor, an immune cell migration factor, a cytokine, an immune system inhibitory factor, a signal-transducing protein, and receptors thereof.

Specific examples of the protein expressed on an immune cell include PD-1, CTLA-4, TIM3, Foxp3, CD3, CD4, CD8, CD25, CD27, CD28, CD70, CD40, CD40L, CD80, CD86, CD160, CD57, CD226, CD112, CD155, OX40 (CD134), OX40L (CD252), ICOS (CD278), ICOSL (CD275), 4-1BB (CD137), 4-1BBL (CD137L), 2B4 (CD244), GITR (CD357), B7-H3 (CD276), LAG-3 (CD223), BTLA (CD272), HVEM (CD270), GITRL, Galectin-9 (Galectin-9), B7-H4, B7-H5, PD-L2, KLRG-1, E-Cadherin, N-Cadherin, R-Cadherin, IDO, TDO, CSF-1R, HDAC, CXCR4, FLT-3, and TIGIT.

Examples of the protein expressed on a stromal cell include a growth factor, a cell adhesion factor, a cell differentiation factor, a blood coagulation factor, an enzyme, a regulator, a cell inducer, a protein inducer, and receptors thereof.

Specific examples of the protein expressed on a stromal cell include CD140a, CD106, CD109, CD140a, CD140b, CD141, CD142, CD143, CD144, CD145, CD146, CD147, CD201, CD202, CD280, CD299, CD309, CD322, CD331, CD332, CD333, CD334, and CD339.

The step (c) in the present invention is preferably carried out by immunostaining using a PID from a viewpoint that a target molecule of the ADC is observed in a "quantitative" manner but not in a "qualitative" manner. Herein, the PID may be bound to an IgG (which is referred to herein as "antibody C") that specifically recognizes and binds to the target molecule of the ADC and used as a stain. Alternatively, the PID may be bound to an IgG (antibody C') that specifically recognizes and binds to the antibody C and used as a stain.

The "qualitative" method indicates that the method correlates with, for example, an expression level of a protein and the number of cells expressed but does not directly deal with them or with an index closely related to them. In the "qualitative" method, certain numbers or indexes within a predetermined range are collectively represented by one score, and the score is ranked on a scale of several numbers, for example, 2 to 5. Accordingly, the "qualitative" method typically depends on subjective and empirical factors of an observer. For example, the following method corresponds to the "qualitative" method: IHC which employs DAB staining for HER2 protein expressed on a cell membrane such as a breast cancer cell and in which assessment is performed based on stainability on cancer cell membranes and staining intensity (staining pattern) of the cancer cell membranes on a 4-point scale, that is, 3+, 2+, 1+, and 0 ("HER2 testing guidelines third edition" Trastuzumab Academy of Pathology, Inc., September 2009). Herein, 3+ represents positive (when the number of cancer cells having a cell membrane stained positively, strongly, and completely >30%); 2+ represents equivocal (when the number of cancer cells having a cell membrane stained completely but weakly or moderately ≥10%, or when the number of cancer cells having a cell membrane stained strongly and completely ≥10% and ≤30%); 1+ represents negative (when the number of cancer cells having a cell membrane stained slightly or almost invisibly ≥10%, and when those cancer cells are partially stained at the cell membrane); and 0 represents negative (when any cell membrane is not positively stained, or when the number of cancer cells having a cell membrane stained positively >10% (positive staining localized in a cell membrane is not eligible for determination)). The following method also corresponds to the "qualitative" method: the method recited in Jager et al., Patient-derived bladder cancer xenografts in the preclinical development of novel target therapies. Oncotarget, Vol. 6, No. 25, 21522-21532, page 21527, FIG. 3. In this method, an expression level of a protein is represented by four scores based on stain images obtained by IHC.

On the other hand, the "quantitative" method indicates that the method directly deals with an expression level of a protein and the number of cells expressed or an index closely related to them, and that the method typically relies on objective measurement results using a device. In the "quantitative" method, typically, a protein of interest is labeled and quantified using a nanosized particle such as a fluorescent nanoparticle, that is, a quantum dot (not integrated) or a phosphor integrated dot (PID). Particularly, the "quantitative" method preferably employs a PID (the method may be referred to herein as "PID method"). A basic embodiment of the PID method is known from Patent Literature 1, Patent Literature 2, or other Patent Literatures and non-Patent Literatures. In the present invention, the PID method may be carried out according to an embodiment base on, for example, a pathological diagnosis using a specimen slide.

It is preferred that the ADC constituent antibody, antibody A, antibody B, antibody C, and antibody C' should all be monoclonal antibodies. The type of animals that produce antibodies (immune animals) is not particularly limited and may be selected from mice, rats, guinea pigs, rabbits, goats, and sheep, as in the related art.

The ADC constituent antibody, antibody A, antibody B, antibody C, and antibody C' may not be natural full-length antibodies and may be antibody fragments or derivatives as long as they are competent to specifically recognize a specific substance of interest (for example, the target molecule of the ADC for the ADC constituent antibody, and the ADC constituent drug for the antibody A) and competent to bind thereto. In other words, the term "antibody" herein includes not only full-length antibodies but also antibody fragments such as Fab, F(ab)'2, Fv, and scFv and derivatives such as chimeric antibodies (humanized antibodies or the like) and multifunctional antibodies.

Through the step (a) and/or step (b), localization of the ADC in a sample is measured. The step (c) in the present invention enables identification of how much the target cell of the ADC expresses the target molecule. Furthermore, measurement of a distance between the ADC and the target molecule enables assessment of how much the ADC and the target molecule actually interact. For example, a distance between a PID stain (such as a bright spot of a PID) that labels the ADC constituent drug and/or the ADC constituent antibody and a bright spot of a PID stain that labels a target protein of the ADC may be measured by the after-mentioned image processing and regarded as a distance between the ADC and the target cell. To carry out this step, immunostaining for the former fluorescent labeling and immunostaining for the latter fluorescent labeling (multiple immunostaining) may be conducted on the same sample (such as a tissue section). Furthermore, it is preferable to employ a PID stain including PIDs that emit different wavelengths of fluorescence to distinguish one from the other.

<Phosphor Integrated Dot>

The PID used in the present invention is a nanosized particle having a structure in which an organic or inorganic particle serving as the matrix contains a plurality of phosphors (for example, fluorochromes) and/or has a surface that adsorbs the phosphors. Herein, it is preferable that the matrix (for example, resin) and fluorescent substances should have substituents or sections with opposite charges and should cause electrostatic interactions.

Being irradiated with an electromagnetic wave (X-ray, UV ray, or visible ray) having a predetermined wavelength, the "phosphor" herein absorbs the energy of the electromagnetic wave to excite electrons and emits extra energy as an electromagnetic wave when returning from the excited state to the ground state. In short, the "phosphor" is a "fluorescent" material, representing a material that directly or indirectly binds to a biological substance-recognizing substance (for example, biotin, avidin, or an antibody; a material that specifically recognizes a biological substance). The "fluorescent" has a broad meaning, including narrowly-defined fluorescence with a short emission lifetime and phosphorescence with a long emission lifetime which enables duration of light emission even when irradiation of an electromagnetic wave for excitation is stopped.

With regard to a matrix included in a PID, examples of organic matters include resins generally classified as thermosetting resins such as melamine resin, urea resin, aniline resin, guanamine resin, phenol resin, xylene resin, and furan resin; resins generally classified as thermoplastic resins such as styrene resin, acrylic resin, acrylonitrile resin, AS resin (acrylonitrile-styrene copolymer), and ASA resin (acrylonitrile-styrene-methyl acrylate copolymer); other resins such as polylactic acid; and polysaccharides, and examples of inorganic matters include silica and glass.

Semiconductor Integrated Nanoparticle

A semiconductor integrated nanoparticle has a structure in which a semiconductor nanoparticle as a phosphor is contained in the aforementioned matrix and/or adsorbed on a surface thereof. A material included in the semiconductor nanoparticles is not particularly limited. Examples of the material include those containing II-VI compounds, III-V compounds, or group-IV elements such as CdSe, CdS, CdTe, ZnSe, ZnS, ZnTe, InP, InN, InAs, InGaP, GaP, GaAs, Si, and Ge. In a case where the matrix contains a semiconductor, the semiconductor may be dispersed in the matrix and may or may not chemically bind to the matrix.

Fluorochrome Integrated Nanoparticle

A fluorochrome integrated nanoparticle has a structure in which a fluorochrome as a phosphor is contained in the aforementioned matrix and/or adsorbed on a surface thereof. The fluorochrome is not particularly limited. Examples of the fluorochrome include rhodamine dye molecules, squafylium dye molecules, cyanine dye molecules, aromatic ring dye molecules, oxazine dye molecules, carbopyronine dye molecules, and pyromecene dye molecules. Alternatives are Alexa Fluor (registered trademark of Invitrogen) dye molecules, BODIPY (registered trademark of Invitrogen) dye molecules, Cy (registered trademark of GE Healthcare) dye molecules, DY (registered trademark of DYOMICS) dye molecules, HiLyte (registered trademark of AnaSpec, Inc.) dye molecules, DyLight (registered trademark of Thermo Scientific) dye molecules, ATTO (registered trademark of ATTO-TEC) dye molecules, and MFP (registered trademark of Mobitec) dye molecules. Note that the generic terms of such dye molecules are named based on the main structure (skeleton) of compounds or based on the registered trademarks, and those skilled in the art may properly understand which fluorochrome belongs to which dye molecule without excessive trial and error. In a case where the matrix contains a fluorochrome, the fluorochrome may be dispersed in the matrix and may or may not chemically bind to the matrix.

A PID is prepared according to a known method (see, for example, JP 2013-57937 A).

More specifically, for example, a fluorescent substance-containing silica particle that includes silica as the matrix and fluorescent substances contained in the matrix may be prepared by the following manner: fluorescent substances such as inorganic semiconductor nanoparticles and organic fluorochromes and a silica precursor such as tetraethoxysilane are dissolved in a solution, and the solution is dripped into a solution containing ethanol and ammonia dissolved so as to hydrolyze the silica precursor.

With regard to a fluorescent substance-integrated resin particle that includes resin as the matrix and fluorescent substances adsorbed on a surface of the resin particle or contained therein, such a resin particle is prepared by procuring a solution of the resin or a dispersion of fine particles in advance; by adding fluorescent substances such as inorganic semiconductor nanoparticles and organic fluorochromes to the solution or the dispersion; and by stirring the mixture. Alternatively, a fluorescent substance-containing resin particle may be prepared by proceeding a polymerization reaction after adding fluorochromes to a solution of a resin raw material. For example, when a thermosetting resin such as melamine resin is used as the matrix, an organic fluorochrome-containing resin particle is prepared by heating a mixture containing a raw material of the resin (monomer, oligomer, or prepolymer: for example, methylolmelamine which is a condensate of melamine and formaldehyde), organic fluorochromes, and preferably, a surfactant and a polymerization reaction accelerator (such as an acid); and by proceeding a polymerization reaction by emulsion polymerization. When a thermoplastic resin such as a styrene copolymer is used as the matrix, an organic fluorochrome-containing resin particle is prepared by heating a reaction mixture containing a raw material of the resin, organic fluorochromes (as a monomer of raw material of the resin, a monomer to which organic fluorochromes are linked by a covalent bond may be used), and a polymerization initiator (such as benzoyl peroxide and azobisisobutyronitrile); and by proceeding a polymerization reaction by radical polymerization or ion polymerization.

Besides the aforementioned semiconductor nanoparticles and the fluorochromes, an example of the fluorescent substances contained in a PID includes a "high-persistence phosphor" that contains $Y_2O_3$ or $Zn_2SiO_4$ as the matrix and $Mn^{2+}$ or $Eu^{3+}$ as an activator agent.

An average particle size of a PID (particularly, a resin particle containing a fluorochrome obtained by the aforementioned production method) is not particularly limited as long as the PID has a particle size appropriate for immunostaining a specimen slide. However, to facilitate detection of a PID as a bright spot, a PID usually has a particle size of 10 to 500 nm, and preferably 50 to 200 nm. Furthermore, a coefficient of variation that indicates the variation of the particle size is usually 20% or less, and preferably 5 to 15%. A PID that satisfies such conditions may be produced by adjusting manufacturing conditions. For example, in producing a PID by emulsion polymerization, the particle size is controlled by an amount of surfactant added. In general, a larger amount of surfactant relative to an amount of matrix raw material in the PID tends to decrease the particle size, and a smaller amount of surfactant tends to increase the particle size.

It should be noted that an electron micrograph of a PID may be imaged with a scanning electron microscope (SEM) to measure a cross-sectional area of the PID, and assuming that the cross-sectional shape is a circle, the diameter of the circle corresponding to the cross-sectional area may be determined as the particle size of the PID. With regard to an average particle size and a coefficient of variation of a group including a plurality of PIDs, an average particle size is determined by calculating particle sizes of a sufficient number of fluorescent substance-integrated nanoparticles (for example, 1000 PIDs) in the aforementioned manner and then by calculating an arithmetic average of those sizes, and a coefficient of variation is determined according to the following expression: 100× standard deviation of particle size/average particle size.

<Component of PID Stain>

[Antibody]=[PID] is an example of a PID stain for fluorescent labeling of an ADC constituent drug, an ADC constituent antibody, or a target molecule of an ADC. For example, [anti-ADC constituent drug antibody]=[PID] is used as a PID stain for staining an ADC constituent drug. Herein, the mode of a bond represented by "=" is not particularly limited. For Examples of the bond include a covalent bond, an ionic bond, a hydrogen bond, a coordinate bond, physical adsorption, or chemical adsorption, and as needed, a linker molecule may be included.

If [antibody]=[PID] having a desired PID preliminarily bound to a desired antibody is commercially available, the present invention may employ such [antibody]=[PID]. Based on a known method that enables a desired fluorochrome to bind to a desired antibody (protein), [antibody]=[PID] may be prepared, for example, using a commercially available fluorescent labeling reagent (kit).

For example, the present invention may employ a silane coupling agent, or a compound widely used to bind an inorganic matter with an organic matter. In this silane coupling agent, one end of a molecule has an alkoxysilyl group that imparts a silanol group by hydrolysis, and the other end has a functional group such as a carboxyl group, an amino group, an epoxy group, or an aldehyde group. Furthermore, the silane coupling agent binds to an inorganic matter through the oxygen atom of the silanol group. Specific examples of the silane coupling agent include mercaptopropyltriethoxysilane, glycidoxypropyltriethoxysilane, aminopropyltriethoxysilane, and one that has a polyethylene glycol chain (for example, PEG-silane no. SIM6492.7; a product of Gelest, Inc.). When using a silane coupling agent, two or more types of agents may be used together.

A reaction procedure of a PID and a silane coupling agent may be a known procedure. For example, silica nanoparticles containing fluorescent substances obtained are dispersed in pure water, and aminopropyltriethoxysilane is added to the solution, and then, the mixture is allowed to react at room temperature for 12 hours. On completion of the reaction, it is possible to obtain silica nanoparticles containing fluorescent substances subjected to surface modification with an aminopropyl group by centrifugation or filtration. Next, an amino group is reacted with a carboxyl group in an antibody to cause an amide bond between the antibody and the silica nanoparticles containing fluorescent substances. As needed, the present invention may employ a condensing agent such as 1-ethyl-3-[dimethylaminopropyl] carboimidide hydrochloride (EDC; a product of Pierce).

The present invention may employ a linker compound having a site that directly binds to silica nanoparticles containing fluorescent substances modified by an organic molecule and a site that binds to a molecular target substance. As a specific example, using sulfosuccinimidyl-4-[N-maleimidomethyl]cyclohexane-1-carboxylate (sulfo-SMCC; a product of Pierce) having both a site that selectively reacts with an amino group and a site that selectively reacts with a mercapto group, an amino group of a silica nanoparticle containing fluorescent substances modified with aminopropyltriethoxysilane is made to bind to a mercapto group of an antibody, whereby yielding a silica nanoparticle containing fluorescent substances to which the antibody is bound.

When binding a biological substance-recognizing substance (a substance that specifically recognizes a biological substance; for example, biotin, avidin, and an antibody) to a polystyrene nanoparticle that contains fluorescent substances, even though the fluorescent substances are fluorochromes or semiconductor nanoparticles, a similar procedure may be applicable. In other words, impregnation of a polystyrene nanoparticle having a functional group such as an amino group with a semiconductor nanoparticle or a fluorescent organic dye yields a fluorescent substance-integrated polystyrene particle having a functional group, and afterwards, using EDC or sulfo-SMCC yields a phosphor-integrated polystyrene particle to which an antibody is bound.

Another example of a PID stain includes [avidin]-[PID] (herein, "-" represents a linkage by a covalent bond which may be mediated by a linker molecule as needed. When using such a PID stain, it is required to preliminarily react [antibody (primary antibody) against substance of interest]-[biotin] with the substance of interest, or to react [primary antibody against substance of interest (primary antibody)] with the substance of interest, and then with [antibody (secondary antibody) against primary antibody against substance of interest]-[biotin].

For example, after staining, the substance of interest and the PID are indirectly connected by the following manner: [substance of interest] . . . [primary antibody against biological substance of interest] . . . [antibody against primary antibody (secondary antibody)]-[biotin]/[avidin]-[PID] (where " . . . " represents a connection by an antigen-antibody reaction, "-" represents a linkage by a covalent bond which may be mediated by a linker molecule as needed, and "/" represents a connection by an avidin-biotin reaction).

Based on a known method that enables biotin to bind to a desired antibody (protein), an antibody-biotin conjugate (biotin-modified antibody) may be prepared using, for example, a commercially available biotin labeling reagent (kit). If a biotin-modified antibody having biotin preliminarily bound to a desired antibody is commercially available, the present invention may employ such an antibody.

Furthermore, based on a known method that enables avidin to bind to a PID, a PID-avidin conjugate (avidin-modified PID) may be prepared using, for example, a commercially available avidin labeling reagent (kit). In this case, avidin may be of modified type such as streptavidin or neutravidin which exerts a higher binding force with biotin than avidin.

The following procedure is a specific example of the method for preparing a PID-avidin conjugate. When a PID includes resin as the matrix, a functional group possessed by the resin and a functional group possessed by avidin (protein) may bind to each other by mediating, as needed, a linker molecule such as PEG, a molecule that possesses functional groups at both ends. For example, when a PID includes melamine resin, a functional group such as an amino group may be used. Alternatively, when a PID includes acrylic resin or styrene resin, copolymerization of a monomer having a functional group (for example, an epoxy group) at a side chain makes it possible to use the functional group or a functional group converted from the functional group (for example, an amino group produced by reacting with ammonia water), and furthermore, to introduce another functional group using those functional groups. In addition, in a case where a fluorescent nanoparticle is a PID or an inorganic semiconductor nanoparticle having silica as the matrix, surface modification by a silane coupling agent makes it possible to introduce a desired functional group. For example, using aminopropyltrimethoxysilane enables introduction of an amino group. On the other hand, for example, a thiol group may be introduced to avidin by reacting N-succinimidyl S-acetylthioacetate (SATA) with the amino group of avidin. Using a crosslinker reagent that includes N-hydroxysuccinimide (NHS) ester having reactivity with an amino group and a maleimide group having reactivity with a thiol group at both ends of a polyethylene glycol (PEG) chain, it is possible to connect a phosphor having an amino group with avidin to which a thiol group is introduced.

In the present invention, staining is performed with a PID staining solution obtained by diluting a PID stain with a diluted solution. Selection of the diluted solution and the dilution ratio may be optimized according to the affinity between a substance of interest and an immunostain.

<Immunostaining>

Hereinafter, an example of immunostaining in cancer cells will be described in detail as Example of the present invention. The immunostaining herein employs a PID and a sample derived from a tumor tissue, specifically, a tissue section (specimen slide).

A "substance of interest" used in the immunostaining according to the present invention is at least one of, or preferably both of, a drug (ADC constituent drug) which is a component of an ADC and an antibody (ADC constituent antibody) which is a component of the ADC. In addition, it is preferable that a target molecule of the ADC should be the "substance of interest" used in the immunostaining.

The "tumor tissue" may be derived from a human (cancer patient) tumor or from a non-human animal tumor.

The "sample derived from a tumor tissue" refers to, for example, a lesion collected from a tumor tissue and a cell obtained by incubating a tumor cell contained in the collected lesion. A typical mode of the "sample derived from a tumor tissue" is a specimen slide prepared according to a predetermined procedure as those commonly used when an expression level of a protein of interest is assessed by immunostaining. Using such a sample, the method for detecting a component of an ADC according to the present invention is carried out in vitro with respect to a human or non-human animal.

A method for preparing a tissue section (which is also simply referred to herein as "section" including a pathological section and the like) and a specimen slide on which the tissue section is mounted is not particularly limited, and the method may employ those prepared by a known method.

(1. Pretreatment of Specimen Slide)

(1-1. Deparaffinization)

A section is immersed in xylene put in a container for deparaffinization. The temperature is not particularly limited but may be at room temperature. The immersion time is preferably 3 minutes or more and 30 minutes or less. As needed, xylene may be replaced during immersion.

The section is then immersed in ethanol put in a container so as to remove xylene. The temperature is not particularly limited but may be at room temperature. The immersion time is preferably 3 minutes or more and 30 minutes or less. As needed, ethanol may be replaced during immersion.

The section is immersed in water put in a container so as to remove ethanol. The temperature is not particularly limited but may be at room temperature. The immersion time is preferably 3 minutes or more and 30 minutes or less. As needed, water may be replaced during immersion.

(1-2. Activation)

According to a known method, a substance of interest is activated. Conditions on activation are not particularly limited. An activating solution used herein may be a 0.01 M citrate buffer solution (pH 6.0), a 1 mM EDTA solution (pH 8.0), 5% urea, or a 0.1 M tris hydrochloride buffer solution. A heating machine used herein may be a microwave, a pressure cooker, or a water bath. The temperature is not particularly limited but may be at room temperature. The temperature may be at 50 to 130° C., and the time may be 5 to 30 minutes.

The activated section is then immersed in PBS put in a container and washed. The temperature is not particularly limited but may be at room temperature. The immersion time is preferably 3 minutes or more and 30 minutes or less. As needed, PBS may be replaced during immersion.

(2. Immunostaining)

In immunostaining, an immunostaining solution in which a stain having a site that binds directly or indirectly to a substance of interest is dispersed in a diluted solution in order to stain an ADC and a target molecule of the ADC. Such an immunostaining solution is placed on a tissue section and made to react with the substance of interest. The immunostain or the diluted solution for diluting the same and other components are as described above and may be prepared in advance before this step.

For example, in an embodiment where [avidin]-[PID] is used as an immunostain and where the substance of interest and the labeling material after staining are [substance of interest] . . . [primary antibody against substance of interest] . . . [antibody against primary antibody (secondary antibody)]-[biotin]/[avidin]-[PID] (where " . . . " represents a connection by an antigen-antibody reaction, "-" represents a linkage by a covalent bond which may be mediated by a linker molecule as needed, "/" represents a connection by an avidin-biotin reaction), first, a specimen slide may be immersed in a solution of the primary antibody (primary reaction), then, a pathological specimen may be immersed in a solution of the secondary antibody-biotin conjugate (secondary reaction), and finally, a tissue section or the pathological specimen may be immersed in a PID staining solution (PID labeling).

Conditions under which the immunostaining is performed, for example, the temperature and immersion time for immersing the specimen slide in a predetermined solution (reagent) in each process, the primary reaction, secondary reaction, and fluorescent labeling, may be appropriately adjusted to obtain an appropriate signal according to immunostaining in the related art.

The temperature is not particularly limited but may be at room temperature. The reaction time is preferably 30 minutes or more and 24 hours or less.

Before the primary reaction, it is preferable to drip a known blocking agent such as BSA-containing PBS or a surfactant such as Tween20.

(3. Posttreatment of Specimen)

The immunostained specimen slide is preferably subjected to treatments such as fixation and dehydration, clearing, and mounting to create an optimum condition for observation.

With regard to fixation and dehydration, the specimen slide may be immersed in a fixing solution (a cross-linker such as formalin, paraformaldehyde, glutaraldehyde, acetone, ethanol, and methanol). With regard to clearing, the specimen slide after the fixation and dehydration may be immersed in a clearant (such as xylene). With regard to mounting, the specimen slide after the clearing may be immersed in a mountant. Conditions for performing these treatments, for example, the temperature and immersion time when immersing the specimen slide in a predetermined treatment solution, may be appropriately adjusted to obtain an appropriate signal according to immunostaining in the related art.

(4. Optional Step)

The present invention may, as needed, include staining for morphological observation which enables bright-field observation of the morphology of cells, tissues, organs and the like. The staining for morphological observation may be performed according to a method in the related art. Morphological observation of tissue specimens normally employs staining using eosin with which cytoplasm, stromata, various strands, red blood cells, and keratinocytes are stained red or dark red. Furthermore, morphological observation normally employs staining using hematoxylin with which cell nuclei, calcium-containing tissues, cartilage tissues, bacteria, and mucus are stained blue or pale blue (hematoxylin/eosin staining (HE staining) is known as a technique to simultaneously perform these two types of staining). In a case where the present invention includes the staining for morphological observation, the step may be performed after or before the immunostaining.

(5. Assessment)

(5-1. Observation and Imaging)

In observation and imaging, the specimen sample is irradiated with excitation light corresponding to PIDs fluorescently labeling the substance of interest in the immunostaining and another excitation light corresponding thereto in the same field of view of a microscope at desired magnification, whereby observing and capturing immunostaining images obtained by fluorescence from those PIDs. Irradiation of excitation light may be performed, for example, with a laser source provided in a fluorescence microscope and an optical filter for excitation light that selectively transmits a predetermined wavelength as needed. In immunostaining with a plurality of immunostains containing different PIDs, different types of filter sets respectively corresponding to the PIDs are changed during observation. Immunostaining images may be captured, for example, by a digital camera provided in a fluorescence microscope. In capturing an immunostaining image, using an optical filter for fluorescence that, as needed, selectively transmits a predetermined wavelength makes it possible to capture an immunostaining image which includes fluorescent of interest and which excludes fluorescent which is not of interest or excitation light noise and other types of light.

(5-2. Image Processing and Signal Measurement)

In image processing and measurement, with respect to an immunostaining image captured for the substance of interest, based on the image processing, a fluorescent labeling signal corresponding to the substance of interest is measured to identify a fluorescent labeling signal corresponding to the substance of interest within the region of a cell membrane. It is preferable to treat the fluorescent labeling signal as the number of fluorescent bright spots.

An example of software used for image processing includes "ImageJ" (open source). Such image processing software enables extraction of bright spots of a predetermined wavelength (color) from the immunostaining image to calculate total luminance of the bright spots or enables measurement of the number of bright spots having predetermined luminance or more, and particularly enables quick and semi-automatic processing for perform the aforementioned embodiment.

Being derived from one fluorescent nanoparticle, a bright spot has a constant size and is observable by a microscope. A signal having a value larger than a fixed value (for example, an average of observed fluorescent nanoparticles) is determined as an integrated bright spot. With software, a bright spot and an integrated bright spot are identified promptly and semi-automatically.

<Method for Acquiring Information>

Using a sample collected from a human or non-human animal subjected to administration of an ADC, a method for acquiring information according to the present invention specifies information associated with, for example, the ADC, a target molecule of the ADC, and a cell contained in the sample.

Examples of the sample include a lesion collected from a disordered human or non-human animal, and a cell obtained by incubating a tumor cell contained in the collected lesion. A typical mode of the sample is a specimen slide prepared according to a predetermined procedure.

The "disorder" is not particularly limited, and examples of the disorder include a neurological disorder, an infectious disorder, a hereditary disorder, and a tumor (cancer). Typically, the disorder is a tumor (cancer). The "tumor" is not particularly limited, and examples of the tumor include solid cancers such as cytoma, melanoma, sarcoma, brain tumor, head and neck cancer, gastric cancer, lung cancer, breast cancer, liver cancer, colon cancer, cervical cancer, prostate cancer, and bladder cancer; leukemia; lymphomas; and multiple myelomas.

An example of the "non-human animal" includes an experimental animal, typically, a tumor-bearing animal, and preferably, a tumor-bearing mouse.

A tumor-bearing mouse are broadly classified into three groups: mouse with a spontaneous and induced tumor, mouse implanted with an incubated cancer cell, and mouse implanted with a patient tumor tissue (see the following table; Kohrt et al., Defining the optimal murine models to investigate immune checkpoint blockers and their combination with other immunotherapies. Annals of Oncology 00: 1-9, 2016).

TABLE 1

| | Cancer cell | Immune cell | Model |
|---|---|---|---|
| Mouse with a spontaneous and induced tumor | Mouse | Mouse | Classic model implanted with a compound<br>*Genetic-engineered mouse model<br>*Human KI mice |
| Mouse implanted with an incubated cancer cell | Mouse<br>Human | Mouse<br>Mouse | (3) Syngeneic murine model<br>(4) Cell-line derived xenograft (CDX) |
| Mouse implanted with a patient tumor tissue | Human | Mouse | (5) Patient derived xenograft (PDX)<br>(6) Immuno-avatar mice<br>(7) Hemato-lymphoid humanized mice<br>(8) Immune-PDX |

*Gene knock-in mice

The experimental animal herein includes a zero-generation experimental animal implanted with a tumor (cancer) tissue collected from a human (cancer patient) or implanted with a human derived tumor cell established as an incubated cell line, and includes a n-generation experimental animal (n 1) implanted with a tumor tissue grown or proliferated inside the body of an n-1 generation experimental animal originated from a tumor tissue or the tumor tissue implanted in the zero-generation experimental animal. Such an experimental animal may be prepared by a known technique. For example, when using a mouse, prepare various types of tumor-bearing mouse models may be prepared, for example, a cell-line derived xenograft (CDX) model mouse, a patient derived xenograft (PDX) model mouse, an Immunno-avatar model mouse, a hemato-lymphoid humanized model mouse, and an immune-PDX model mouse. Furthermore, the present inventors have created an environment for purchasing premade tumor-bearing mouse models. However, a tumor-bearing mouse model implanted with an incubated cell derived from a tumor cell taken out of a patient is more classic and easier to prepare.

The contents of the "information for diagnosis or treatment" in the present invention is not particularly limited. The contents of the "information for diagnosis or treatment" may be information relative to diagnosis, for example, how an expression level of a target molecule is changed by administration of an ADC, or how the progress of a disorder (a state of a disorder and the like) changes, and may be information relative to diagnosis, for example, how effective the ADC is to the disorder.

The method for acquiring information for diagnosis or treatment of a disorder according to the present invention (which may be simply referred to as "method for acquiring information according to the present invention") identifies and combines at least one piece, preferably two or more pieces, of information selected from, for example, localization of an ADC in a sample, localization and an expression level of a target molecule of the ADC, a distance between the ADC and the target molecule, the type, the number, and the morphology of a cell that expresses the target molecule, an expression level, a expressing site, distribution, and an appropriative area of the target molecule per unit area in a tissue, inside a lesion, or on a cell, histogram and curve representing the expression level of the target molecule per cell and the number of cells corresponding to the expressed target molecules, and the size of a lesion such as a tumor.

(i) Localization of the ADC is identified by immunostaining an antibody and/or a drug which are components of the ADC in the sample (specimen slide) and by observing and capturing a dark-field image of the sample while irradiating the sample with excitation light that has a predetermined wavelength corresponding to a PID, whereby obtaining an image in which a PID of a stain that labels the antibody and/or drug which are components of the ADC is expressed as bright spots.

Herein, another staining may be performed to identify the morphology of a cell with a stain for morphological observation (for example, eosin).

Together with the dark-filed image, when an image which is stained to express the shape of a cell is obtained by bright-field observation and imaging, superimposing these two images by image processing enables observation of a positional relation between individual cells and the ADC contained in the whole image or in a specific region of the image (for example, only in a tumor tissue).

(ii) In order to specify a ratio of a target molecule bound to the ADC to the total amount of target molecules, the first step is to obtain an image, in a manner similar to (i), in which a PID that labels a target molecule is expressed as a bright spot, and the next step is to count the number of bright spots that represent target molecules expressed on a cell captured in this image or in a specific region of this image (for example, only in a tumor tissue). Furthermore, it is possible to identify a ratio of a target molecule bound to the ADC to the total amount of target molecules by superposing this image by image processing on an image in which the PID that labels the antibody and/or drug which are components of the ADC is expressed as a bright spot, and by counting the number of bright spots each representing the PID that labels the antibody and/or drug which are components of the ADC and the number of bright spots each representing the PID that labels the target molecule, and then by calculating a proportion of those number with respect to the number of bright spots that represent target molecules.

(iii) Still further, it is possible to observe a distance between the target molecule in the whole image or in a specific region (for example, only in a tumor tissue), the antibody which is a component of the ADC, and the drug which is a component of the ADC by obtaining and superposing the following three images: an image in which the PID that labels the target molecule is expressed as a bright spot, an image in which the antibody which is a component of the ADC is expressed as a bright spot, and an image in which the PID that labels the drug which is a component of the ADC is expressed as a bright spot.

In addition to (i) to (iii), for example, performing staining for morphological observation in combination with fluorescence immunostaining of a target molecule enables quantification of an average expression level per target cell of the target molecule for all cells contained in the image. In this case, after the expression level is determined in a manner similar to (ii), the expression level may be divided by the number of cells contained in a specific region of the image. Herein, the number of bright spots of the PID labeling the target molecule may be used as an index of an expression level of a bright spot target molecule. Alternatively, the brightness (luminance or fluorescence intensity) of a certain bright spot may be divided by the separately measured brightness of another PID so as to calculate the number of PIDs included in the bright spot, and the obtained number of particles may be used as an index of an expression level of the target molecule. When creating a histogram or a curve represented by expression levels and the number of corresponding cells, an expression level of a target molecule per cell per may be plotted every predetermined number or continuously on the abscissa, and the number of cells (frequency) corresponding to the expression levels may be calculated and plotted on the ordinate.

Such a histogram and curve provide information relative to, for example, a distribution pattern of target molecules (a shape of the histogram or curve, the number of peaks), an average or median, and a value of the variance (CV). Particularly, creating a histogram provides information showing that the number of bright spots or the number of particles per cell becomes the largest at what number of cells (frequency).

By comparing such information before and after administration of the ADC with test results such as the efficacy of the ADC (for example, changes in size and state of a lesion by administration) and localization of the ADC, and a distance between the ADC and the target molecule, it is possible to analyze and understand what information the efficacy of the ADC is most related to, in other words, what information the prediction of the efficacy should be based on.

EXAMPLES (Preparation of Biotin-Modified Anti-Rabbit IgG Antibody)

In a 50 mM Tris solution, 50 µg of an anti-rabbit IgG antibody used as a secondary antibody was dissolved. To this solution, a dithiothreitol (DTT) solution was added, and then mixed and allowed to react at 37° C. for 30 minutes so that the final concentration of the solution became 3 mM. The reaction solution was then made to pass a desalting column "Zeba Desalt Spin Columns" (Thermo Scientific, Cat. #89882), whereby purifying the secondary antibody reduced by DTT. In a 50 mM Tris solution, 200 µL of total amount of the purified antibody was dissolved to prepare an antibody solution. At the same time, a linker reagent "Maleimide-PEG2-Biotin" (Thermo Scientific, product number 21901) was adjusted to 0.4 mM by DMSO. This linker reagent solution in an amount of 8.5 µL was added to the antibody solution, and then mixed and allowed to react at 37° C. for 30 minutes so that biotin bound to the anti-rabbit IgG antibody through a PEG chain. The reaction solution was purified through a desalting column. The concentration of a protein (biotin-modified IgG antibody) in the reaction solution was calculated by measuring, with a spectrophotometer (F-7000; a product of Hitachi), the absorbance of the desalted reaction solution at a wavelength of 300 nm. A solution in which the concentration of the biotin-modified IgG antibody was adjusted to 250 µg/mL with a 50 mM Tris solution was used as a solution of a biotin-modified secondary antibody.

[Exemplary Preparation 1] Preparation of Red PID Stain (Preparation of Texas Red Dye-Integrated Melamine Resin Particle)

After dissolving 2.5 mg of a Texas Red dye molecule "Sulforhodamine 101" (Sigma-Aldrich) in 22.5 mL of pure water, the solution was stirred with a hot stirrer for 20 minutes while the temperature of the solution was maintained at 70° C. To the stirred solution, 1.5 g of melamine resin "Nicalac MX-035" (Nippon Carbide Industries Ltd.) was added, and the mixture was further heated and stirred for 5 minutes under the same conditions. To the stirred solution, 100 µL of formic acid was added, and the mixture was stirred for 20 minutes while the temperature of the solution was maintained at 60° C. The solution was then allowed to cool to room temperature. The cooled solution was dispensed into a plurality of tubes for centrifugation and centrifuged at 12,000 rpm for 20 minutes to precipitate Texas Red dye-containing melamine resin particles contained in the solution as a mixture. Supernatants were removed and precipitated particles were washed with ethanol and water. About 1000 resin particles obtained were observed by SEM, and an average particle diameter was measured in the aforementioned manner. The average particle diameter was 152 nm. The Texas Red dye-containing melamine resin particles thus prepared was subjected to surface modification according to the following procedure.

(Preparation of Streptavidin-bound Texas Red Dye-containing Melamine Resin Particle)

In 1.5 mL of EtOH, 0.1 mg of the particles obtained were dispersed, and 2 µL of aminopropyltrimethoxysilane LS-3150 (Shin-Etsu Chemical Co., Ltd.) was added thereto and allowed to react for 8 hours, whereby performing surface amination.

Next, phosphate buffered saline (PBS) containing 2 mM ethylenediaminetetraacetic acid (EDTA) was used to adjust the surface aminated particles to 3 nM. SM(PEG)$_{12}$ (succinimidyl-[N-maleimidopropionamido)-dodecaethyleneglycol]ester, a product of Thermo Scientific) was mixed in this solution and allowed to react for 1 hour so that the final concentration of the solution became 10 mM. The mixture was centrifuged at 10,000 G for 20 minutes. After removing supernatants, PBS containing 2 mM EDTA was added to the mixture to disperse precipitates, followed by another centrifugation. The resultant was washed three time in such a manner, whereby yielding Texas Red-integrated melamine particles having a maleimide group at the end.

At the same time, using N-succinimidyl S-acetylthioacetate (SATA), a thiol group was added to streptavidin (a product of FUJIFILM Wako Pure Chemical Corporation), and then, the streptavidin was filtrated with a gel filtration column so as to yield a streptavidin solution that may bind to the Texas Red-integrated melamine particles.

The Texas Red-integrated melamine particles and streptavidin were mixed in PBS containing 2 mM EDTA and allowed to react at room temperature for 1 hour. The reaction was stopped by adding 10 mM mercaptoethanol. After the resulting solution was condensed with a centrifugal filter, unreacted streptavidin and the like was removed by a gel filtration column for purification to yield streptavidin-bound Texas Red-integrated melamine particles. These melamine particles were used as a red PID stain in Reference Example 1 and Examples 1 to 4.

[Exemplary Preparation 2] Preparation of Green PID Stain

According to the aforementioned procedure (preparation of streptavidin-bound Texas Red-integrated melamine resin particles), FITC was used in place of the Texas Red dye molecule "Sulforhodamine 101" (Sigma-Aldrich) to prepare FITC dye integrated melamine resin particles having an average particle diameter of 159 nm. According to the aforementioned procedure, surface modification of the particles obtained was carried out using an anti-Brentuximab antibody (purified Brentuximab was added to rabbit spleen to make the antibody) in place of streptavidin to prepare melamine resin particles containing an antibody-bound FITC dye. These melamine resin particles were used as a green PID stain in Examples 2 to 4.

[Exemplary Preparation 3] Preparation of Blue PID Stain

According to the aforementioned procedure (preparation of streptavidin-bound Texas Red dye-containing melamine resin nanoparticles), Phenylcoumarin was used in place of the Texas Red dye molecule "Sulforhodamine 101" (Sigma-Aldrich) to prepare melamine resin particles containing Phenylcoumarin dye and having an average particle diameter of 132 nm. According to the aforementioned procedure, surface modification of the particles obtained was carried out using an anti-monomethyl auristatin E (MMAE) mouse monoclonal antibody ("clone 2E2"; Epitope Diagnostics, Inc.) in place of streptavidin to prepare melamine resin particles containing an antibody-bound phenylcoumarin dye. These melamine resin particles were used as a blue PID stain in Examples 2 to 4.

[Reference Example 1] Assessment of Expression Level of CD30

Preparation of Specimens

From SofiaBio LLC, the present inventors bought tissue samples collected from 14 malignant lymphoma patients and implanted the samples into acquired immunodeficient mice, whereby preparing PDX model mice. A 2 mm-square tumor tissue corresponding to each patient was implanted to each mouse subcutaneously. A month later when each tumor tissue grew to about 300 $mm^3$, 100 mg/kg of Brentuximab vedotin (trade name; Adcetris (registered trademark)) was administered to the tail vein of each mouse once a day, and a total of one time. The efficacy of a drug was determined by measuring the volume of each tumor before the initial administration and after 100 days. Furthermore, a part of each tumor was collected by needle biopsy after three days from the administration, and several formalin-fixed paraffin-embedded (FFPE) tissue slides were prepared for each mouse.

(Pretreatment of Specimens)

The FFPE tissue slides prepared were deparaffinized and then washed to substitute for water. Antigens were activated by autoclaving the washed tissue slides in 10 mM citrate buffer solution (pH 6.0) at 121° C. for 15 minutes. The activated tissue slides were washed with PBS, and resulting specimen slides were subjected to blocking for 1 hour with 1% BSA-containing PBS.

(Primary Reaction of Immunostaining)

With regard to a primary reaction to primarily immunostain a biological substance of interest, CD30, PBS containing 1 W/W % of BSA was used to prepare a primary reaction solution containing an anti-CD30 rabbit polyclonal antibody ("GTX55557"; GeneTex, Inc.) in a concentration of 0.05 nM. The specimens prepared in the step "Pretreatment of Specimen" were immersed in this primary reaction solution and allowed to react overnight at 4° C.

(Secondary Reaction of Immunostaining)

Using PBS containing 1 W/W % of BSA, a secondary reaction solution was prepared by diluting the solution containing the biotin-modified anti-rabbit IgG antibody prepared in the step "Preparation of Biotin-modified Anti-rabbit IgG Antibody." The solution was diluted to 6 μg/mL. The specimens after the primary reaction were washed with PBS, and then immersed in the secondary reaction solution, and allowed to react at room temperature for 30 minutes.

(Immuno Staining Labeling-1: DAB Labeling)

The specimens after the secondary reaction were washed with PBS, then immersed in streptavidin-HRP (Thermo Fisher Scientific Inc., 21130), and allowed to react at room temperature for 60 minutes. The specimens were then washed with PBS and immersed in a DAB (3,3'-Diaminobenzidine) solution for 1 minute.

(Immunostaining Labeling-2: PID Labeling)

Using a diluted solution for fluorescent nanoparticles in which casein content (composition=α-casein (Sigma-Aldrich, c6780): 50 W/W %, β-casein (Sigma-Aldrich), c6905):50 W/W %) and BSA content are adjusted to 1% and 3%, respectively, the melamine resin particles containing streptavidin-modified Texas Red dye prepared in the step "Preparation of Red PID Stain" were diluted to 0.02 nM, whereby preparing a fluorescent labeling reaction solution. The specimens after secondary reaction were immersed in this fluorescent labeling solution and allowed to react at room temperature for 3 hours.

The DAB labeling and the PID labeling were performed on separate specimen slides (tissue sections put on both slides were adjacent sections and regarded as the same specimen samples). The following data results of Table 2 show a proportion of positive cells stained by DAB and the number of fluorescent bright spots of the same patient tissues.

(Staining for Morphological Observation)

The fluorescently stained specimen slides were stained with a Mayer's hematoxylin solution for 5 minutes to be subjected to hematoxylin staining, and then washed with running water at 45° C. for 3 minutes.

(Posttreatment of Specimen)

The immunostained specimen slides were immersed in pure ethanol for 5 minutes, and this operation was repeated four times to fix and dehydrate the specimen slides. Next, the specimen slides were immersed in xylene for 5 minutes, and this operation was repeated four times to clear the specimen slides. Finally, a mounting medium "EntellanNew" (Merck) was placed on each specimen, and a cover glass was covered on each specimen to perform mounting, whereby preparing specimens for observation.

Assessment (The Number of Fluorescent Bright Spots)

A fluorescence microscope "BX-53" (Olympus Corporation) was used to observe fluorescence emission, and a digital microscope camera "DP73" (Olympus Corporation) attached to the fluorescence microscope was used to capture immunostaining images (400×).

First, each specimen was irradiated with excitation light corresponding to Texas Red used for the fluorescent labeling of CD30 so as to cause fluorescence emission. Then, immunostaining images in such a state were captured. Herein, an optical filter for excitation light provided in the fluorescence microscope was used to set a wavelength of the excitation light to 575 to 600 nm, and an optical filter for fluorescence was used to set a wavelength of fluorescence to be observed to 612 to 692 nm. The intensity of the excitation light during observation and imaging with the fluorescence microscope was set in such a manner that irradiation energy around the center of a field of view became to 900 $W/cm^2$. The exposure time during imaging was adjusted in a range that made the luminance of each image unsaturated, and the time was set to, for example, 4000 μseconds.

Such immunostaining images were captured in the same field of view. After the field of view was changed to another, the same operation was repeated. In total, five fields of view (first to fifth fields of view) were imaged per specimen Image processing software "ImageJ" (open source) was used for image processing in this step.

Among the bright spots representing the Texas Red-integrated melamine particles obtained by the fluorescent labeling of CD30 in the immunostaining images, the number of bright spots having a predetermined luminance or more was measured. The number was counted and used as an assessment index of an expression level of CD30.

Next, bright-field observation and imaging with the fluorescence microscope were performed to capture staining images obtained by the DAB staining and staining images obtained by the hematoxylin staining for morphological observation of cells.

Such immunostaining images and immunostaining images for morphological observation were captured in the same field of view. After the field of view was changed to another, the same operation was repeated. In total, five fields of view were imaged per specimen slide.

Table 2 shows the results of Reference Example 1. The results show that the more the proportion of positive cells stained by PID increases, due to administration of Adcetris, the more the tumor size tends to decrease and the efficacy of Adcetris (effect of reducing the tumor size) tends to enhance. On the other hand, the results do not show a correlation between the efficacy of Adcetris and the assessment of the expression level of CD30 based on the DAB labeling in the related art.

TABLE 2

|  | Assessment based on DAB (Proportion of positive cells stained by DAB) | Assessment based on PID (Proportion of positive cells stained by PID) | Determination of drug efficacy |
|---|---|---|---|
| Sample A | 0 | 0 | PD |
| Sample B | 0 | 15 | PR |
| Sample C | 0 | 60 | PR |
| Sample D | 10 | 20 | PD |
| Sample E | 10 | 80 | SD |
| Sample F | 30 | 50 | SD |
| Sample G | 40 | 60 | PR |
| Sample H | 50 | 80 | PR |
| Sample I | 60 | 100 | CR |
| Sample J | 80 | 100 | PR |
| Sample K | 80 | 100 | SD |
| Sample L | 80 | 100 | PD |
| Sample M | 100 | 100 | PR |
| Sample N | 100 | 100 | CR |

CR (Complete Response): Disappearance of all lesions lasting for four weeks or more
PR (Partial Response): A decrease supposed to be at least 30% lasting for four weeks or more
PD (Progressive Disease): An increase supposed to be at least 20%, or appearance of a new lesion
SD (Stable Disease): Changes corresponding to neither PR nor PD Example 1 Quantitative Assessment of Antibody-Drug-Conjugate Some tissue slides prepared in Reference Example 1 were used for testing. Specimen slides of each mouse before and after administration were stained and assessed in a manner similar to Reference Example 1 except that an anti-Brentuximab antibody was used instead of the anti-CD30 rabbit polyclonal antibody in the primary reaction.

The DAB labeling, the PID fluorescent labeling for CD30, and the PID fluorescent labeling for Adcetris were performed on separate specimen slides. The following data results of Table 2 show a proportion of positive cells stained by DAB and the number of fluorescent bright spots of the same patient tissues.

With regard to a slide in which Adcetris was fluorescently labeled, a cell having a cell membrane with five or more bright spots was defined as an Adcetris-delivered cell.

Table 3 shows the results of Example 1.

TABLE 3

|  | Assessment based on PID before administration (proportion of Positive cells stained by PID) | Assessment based on PID after administration (proportion of Positive cells stained by PID) | Proportion of Adcetris-delivered cells after administration | Determination of drug efficacy |
|---|---|---|---|---|
| Sample A | 0 | 0 | 0 | PD |
| Sample B | 15 | 10 | 10 | PR |
| Sample C | 60 | 20 | 40 | PR |
| Sample D | 20 | 10 | 0 | PD |
| Sample E | 80 | 0 | 40 | SD |

TABLE 3-continued

|  | Assessment based on PID before administration (proportion of Positive cells stained by PID) | Assessment based on PID after administration (proportion of Positive cells stained by PID) | Proportion of Adcetris-delivered cells after administration | Determination of drug efficacy |
|---|---|---|---|---|
| Sample F | 50 | 10 | 30 | SD |
| Sample G | 60 | 20 | 30 | PR |
| Sample H | 80 | 30 | 50 | PR |
| Sample I | 100 | 0 | 100 | CR |
| Sample J | 100 | 30 | 60 | PR |
| Sample K | 100 | 60 | 20 | SD |
| Sample L | 100 | 100 | 0 | PD |
| Sample M | 100 | 40 | 60 | PR |
| Sample N | 100 | 0 | 100 | CR |

<Perspectives>

In Sample A, CD30, a target protein of Adcetris, is not expressed on a tumor, which predictively shows that even after drug administration the drug is not delivered to a cancer cell and not incorporated by the cancer cell. In this mouse, the tumor is progressing, and the efficacy of Adcetris is not seen. In each of Samples B and C, CD30 is not detected by DAB but is detected by PID, which indicates that CD30 is expressed. In addition, the drug is delivered to a cell, indicating that Adcetris is effective for a tumor in these Samples. In Sample D, although CD30 is detected to be expressed on a low level, the drug is not delivered to a cancer cell. In Sample E, CD30 is widely distributed, and the drug is delivered, but there is no cell that expresses CD30 after administration. Therefore, it is considered that further administration of Adcetris to the Sample E mouse may not produce an effect. In Sample F, CD30 is expressed, and the drug is delivered. With regard to a mouse of Sample F, at the 100th day of administration when a tumor is measured, no change is seen in the tumor size, but since CD30-expressing cells still remain, it is expressed that further administration will produce improvement in drug efficacy. In each of Samples G to J, the drug is delivered to a cell, indicating that Adcetris is effectively acting. In Sample L, CD30 is strongly expressed, but the drug is not delivered to a cancer cell, and no drug effect is seen in the tumor size. In each of Samples M and N, CD30 is strongly expressed, and the drug is delivered. Furthermore, drug effects in both Samples are observed to be prominent.

The results show that there is a correlation between the expression level of CD30 measured by the PID method, the proportion of cells to which the drug is delivered, and the assessment of drug efficacy. Accordingly, utilizing the PID method enables quantification of an expression level of a predetermined protein expressed on an immune cell with high accuracy. In addition, quantification results provide information useful for a dosage regimen for diagnosis or treatment of cancer.

In this Example, bright spots of Adcetris in a cell membrane region were measured based on observation information of the cell morphology. Note that this Example may employ a technique in which bright spots of Adcetris in an intracellular region and bright spots of Adcetris in an extracellular region are measured to obtain information associated with the number and positions of bright spots located in each region, whereby analyzing the information.

Example 2

Each slide prepared in Reference Example 1 was pretreated in a similar manner to Example 1. In a similar manner to Reference Example 1, primary reaction and secondary reaction were performed. Furthermore, the red PID stain prepared in Exemplary Preparation 1 was diluted with 1% BSA-containing PBS to 0.1 nM so as to prepare a solution. The solution was loaded on a specimen slide. After standing overnight, the stained tissue specimen was immersed in a PBS-filled container for 15 minutes. The green PID stain prepared in Exemplary Preparation 2 was diluted with 1% BSA-containing PBS to 0.1 nM and was placed on a specimen slide together with the slide stained with the red PID. After standing overnight, the stained tissue specimen was immersed in a PBS-filled container for 15 minutes. Furthermore, the blue PID stain prepared in Exemplary Preparation 3 was diluted with 1% BSA-containing PBS to 0.1 nM, and the resulting solution was placed on a specimen slide. After standing overnight, the stained tissue specimen was immersed in a PBS-filled container for 30 minutes.

In the above step, after the secondary reaction, the red PID stain, the green PID stain, and the blue PID stain which were adjusted to have a final concentration of 0.1 nM by 1% BSA-containing PBS may be simultaneously placed on the specimen slide. After standing overnight, the stained tissue specimen may be immersed in a PBS-filled container for 15 minutes.

Then, the specimen was post-treated in a manner similar to Reference Example 1, and the immunostained tissue specimen was placed on a stage. Bright spots of each color were observed using the following three types of filter sets (Semrock):green, red, and blue.

Figure 2:
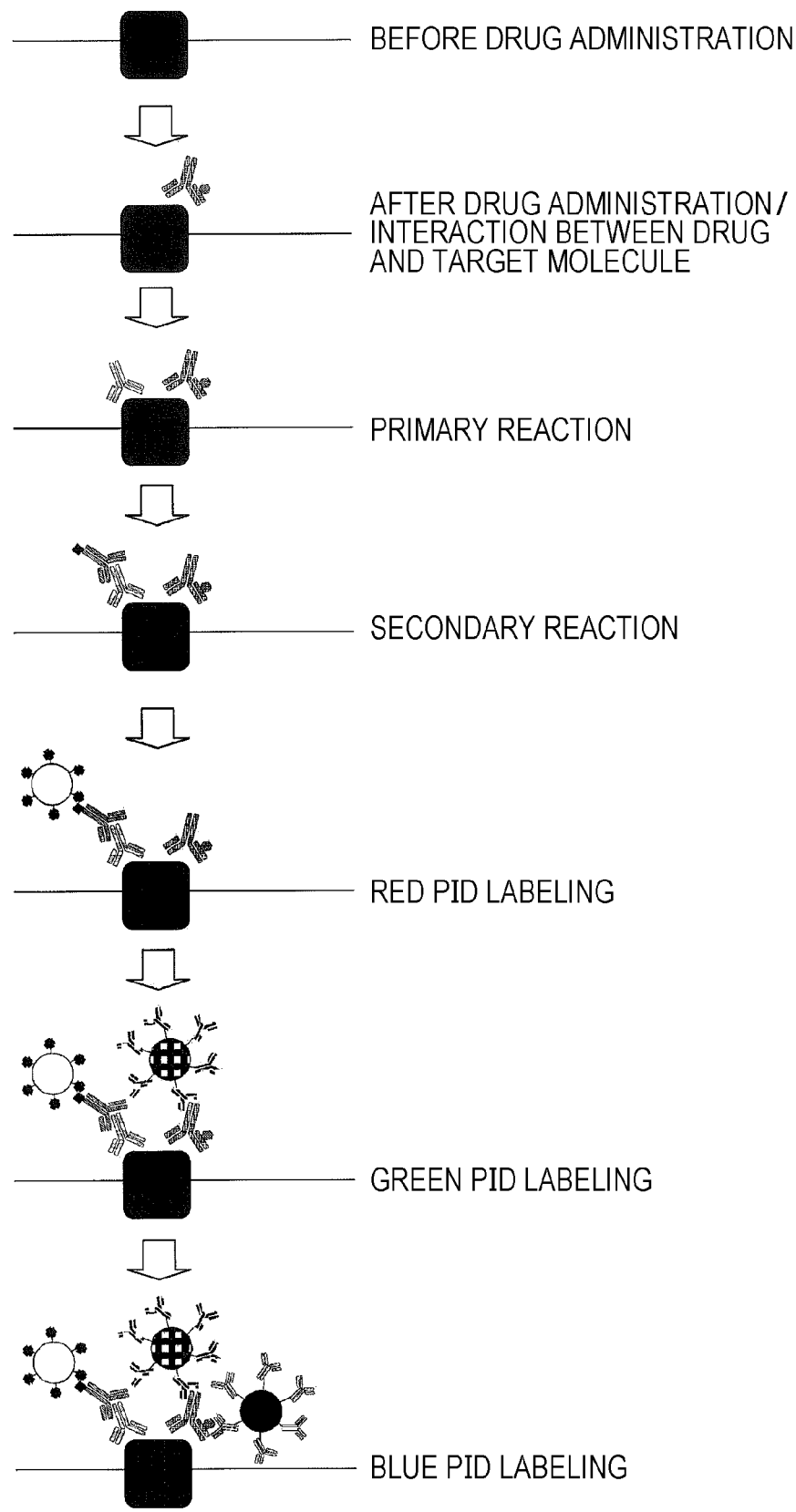
FIG. 2 is a flowchart of the trichrome staining performed in Example 2.

FIG. 1 is a schematic view of trichrome staining performed in Example 2, and FIG. 2 is a flowchart of the trichrome staining.

TABLE 4

| | Excitation Wavelength and Publication Wavelength of Filter Wavelength | | |
|---|---|---|---|
| Filter sets | Red (Texas Red) | Green (FITC) | Blue (Phenylcoumarine) |
| Excitation Filter | 586 nm (wavelength width 20 nm) | 470 nm (wavelength width 30 nm) | 438 nm (wavelength width 24 nm) |

TABLE 4-continued

| | Excitation Wavelength and Publication Wavelength of Filter Wavelength | | |
|---|---|---|---|
| Filter sets | Red (Texas Red) | Green (FITC) | Blue (Phenylcoumarine) |
| Fluorescence Filter | 628 nm (wavelength width 32 nm) | 525 nm (wavelength width 50 nm) | 483 nm (wavelength width 32 nm) |

Every time the filter sets were changed, the number of fluorescent bright spots of a fluorescence image of a tissue specimen was observed, imaged, and subjected to image processing. When bright spots of three colors are seen on an identical cell membrane, a specimen with such a membrane is defined as "Adcetris-delivered cell." The results show that there is a correlation between the Adcetris-delivered cells and the drug assessment. In other words, a position where three bright spots coincide with each other indicates a position where CD30 exists and where non-separated Adcetris (in the state of ADC) exists. It is considered that the accuracy of the assessment of drug efficacy will improve by defining a correct Adcetris-delivered cell, excluding non-specific detection of Adcetris or detection of separated Adcetris.

Note that when observing distribution of bright spots using an anti-drug antibody of an ADC, it is found that a cell having 10 or more bright spots distributed corresponds to CR (complete response).

Furthermore, it becomes clear that a distance between a CD30-expressing cancer cell and Adcetris is quantified as a distance between bright spots. Accordingly, quantification of an expression level of a predetermined protein based on the PID method makes it possible to quantify an expression level of a target molecule on a cancer cell and to measure a distance between the target molecule and an ADC, which enables acquisition of multiple information.

REFERENCE SIGNS LIST

10 CD30
20 Adcetris constituent drug (monomethyl auristatin E)
25 Adcetris constituent antibody (Brentuximab)
30 Anti-monomethyl auristatin E antibody
35 Anti-CD30 antibody
40 Anti-IgG antibody
41 Anti-Brentuximab antibody
50 Biotin
55 Streptavidin
60 Texas Red
61 Phenylcoumarin
62 FITC
70 Linker

The invention claimed is:

1. A method for detecting a component of an antibody-drug-conjugate (ADC) by immunostaining using a phosphor integrated dot (PID), the method comprising:
    immunostaining a drug component of the ADC in a specimen with a first antibody labelled with a first PID, wherein the first antibody binds to the drug component, and the first PID comprises a first phosphor;
    immunostaining an antibody component of the ADC in the specimen with a second antibody labeled with a second PID, wherein the second antibody binds to the antibody component, the second PID comprises a second phosphor, and the first and second phosphors have different emission wavelengths;
    visualizing the drug component of the ADC by irradiating the specimen with a first excitation light for the first phosphor and observing a fluorescence from the first phosphor; and
    visualizing the antibody component of the ADC by irradiating the specimen with a second excitation light for the second phosphor and observing a fluorescence from the second phosphor.

2. The method for detecting a component of an antibody-drug-conjugate according to claim 1, further comprising (c) visualizing a target molecule of the antibody-drug-conjugate.

3. The method for detecting a component of an antibody-drug-conjugate according to claim 1,
    wherein the antibody component of the ADC is capable of binding to a protein expressed on a cell surface of a cancer cell or an immune cell, and
    the drug component of the ADC is selected from the group consisting of vinca alkaloids, taxanes or toxoids, alkylating agents, platinum derivatives, antimetabolites, inhibitors of topoisomerase I or II, L-canavanine, antibiotics, L-asparaginase, hormones, pure inhibitors of aromatase, analogous antagonists of androgen and LH-RH, cytokines, proteasome inhibitors, farnesyl-transferase inhibitors (FTI), epothilone, maytansinoids, discodermolide, fostryesin, antibodies, inhibitors of tyrosine kinase, endostatin, and pharmaceutically acceptable base addition salts or acid addition salts, hydrates, solvates, precursors, metabolites, or stereoisomers thereof.

4. The method for detecting a component of an antibody-drug-conjugate according to claim 2, wherein the target molecule is a protein expressed on a cell.

5. The method for detecting a component of an antibody-drug-conjugate according to claim 2, wherein the target molecule is a receptor or a ligand expressed on a cell surface.

6. The method for detecting a component of an antibody-drug-conjugate according to claim 2, wherein the target molecule is selected from the group consisting of a protein in an immune system, a cancer cell growth factor, a metastasis inhibitory factor, a vascular growth factor, a cytokine, a cancer cell growth inhibitory factor receptor, a metastasis inhibitory factor receptor, a vascular growth factor receptor, and a cytokine receptor in a cancer cell.

7. The method for detecting a component of an antibody-drug-conjugate according to claim 3, wherein the cell is a cancer cell or an immune cell.

8. The method for detecting a component of an antibody-drug-conjugate according to claim 5, wherein the target molecule is selected from the group consisting of a protein in an immune system, a cancer cell growth factor, a metastasis inhibitory factor, a vascular growth factor, a cytokine, a cancer cell growth inhibitory factor receptor, a metastasis inhibitory factor receptor, a vascular growth factor receptor, and a cytokine receptor in a cancer cell.

* * * * *